United States Patent
Cook, III

(10) Patent No.: US 6,602,697 B1
(45) Date of Patent: Aug. 5, 2003

(54) PROCESS FOR PURIFYING HUMAN PAPILLOMAVIRUS VIRUS-LIKE PARTICLES

(75) Inventor: James C. Cook, III, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/762,662

(22) PCT Filed: Aug. 10, 1999

(86) PCT No.: PCT/US99/17930

§ 371 (c)(1),
(2), (4) Date: May 1, 2001

(87) PCT Pub. No.: WO00/09671

PCT Pub. Date: Feb. 24, 2000

Related U.S. Application Data

(60) Provisional application No. 60/096,568, filed on Aug. 14, 1998.

(51) Int. Cl.⁷ ............................... C12N 7/02; C07K 1/22
(52) U.S. Cl. ..................... 435/239; 530/415; 424/224.1
(58) Field of Search ...................... 435/239; 424/204.1; 530/415

(56) References Cited

U.S. PATENT DOCUMENTS

| | | |
|---|---|---|
| 4,612,283 A | 9/1986 | Sugahara et al. |
| 5,085,781 A | 2/1992 | Tsuru et al. |

FOREIGN PATENT DOCUMENTS

| | | | |
|---|---|---|---|
| WO | WO 95/31532 | 11/1995 | |
| WO | 96/09375 | * 3/1996 | ............ C12N/7/00 |
| WO | 96/15247 | * 5/1996 | ............ C12N/15/37 |
| WO | 96/29413 | * 9/1996 | ............ C12N/15/37 |
| WO | 96/30520 | * 10/1996 | ............ C12N/15/37 |
| WO | WO 97/08298 | 3/1997 | |

OTHER PUBLICATIONS

Scopes, Robert K. Protein Purification, Principles and Practise, Second Edition. Springer–Verlag, New York, 1987. pp. 173–176.*

Tsuru, S. et al. "Adsorption and Preparation of Human Viruses Using Hydroxyapatite Column", Bio–Medical Materials and Engineering, 1991, vol. 1, pp. 143–147.

* cited by examiner

*Primary Examiner*—Mary E. Mosher
(74) *Attorney, Agent, or Firm*—Alysia A. Finnegan; Joanne M. Giesser

(57) ABSTRACT

A process for purifying papillomavirus virus-like particles (VLPs) includes the step of passing a partially purified VLP-containing solution through a hydroxyapatite chromatography column. The VLPs are then eluted using a buffer containing phosphate anion. The advantages of this method include the recovery of a high yield of intact VLPs.

9 Claims, No Drawings

PROCESS FOR PURIFYING HUMAN PAPILLOMAVIRUS VIRUS-LIKE PARTICLES

CROSS-REFERENCE TO RELATED APPLICATIONS

This application is a U.S. national application of PCT/US99/17930, filed Aug. 10, 1999 and which published as WO 00/09671, Feb. 24, 2000, and which claims the benefit of U.S. Provisional Patent Application No. 60/096,568, filed Aug. 14, 1998.

FIELD THE INVENTION

This invention relates to a process for making and purifying papillomavirus (HPV) virus-like particles (VLPs), which can be used as a vaccine component.

BACKGROUND OF THE INVENTION

Papillomavirus infections occur in a variety of animals, including humans, sheep, dogs, cats, rabbits, monkeys, snakes and cows. Papillomaviruses infect epithelial cells, generally inducing benign epithelial or fibroepithelial tumors at the site of infection. Papillomaviruses are species specific infective agents; a human papillomavirus cannot infect a nonhuman animal.

Papillomaviruses may be classified into distinct groups based on the host that they infect. Human papillomaviruses (HPV) are further classified into more than 70 types based on DNA sequence homology (for a review, see Papillomaviruses and Human Cancer, H. Pfister (ed.), CRC Press, Inc., 1990). Papillomavirus types appear to be type-specific immunogens in that a neutralizing immunity to infection to one type of papillomavirus does not confer immunity against another type of papillomavirus.

Papillomaviruses are small (50–60 nm), nonenveloped, icosahedral DNA viruses that encode for up to eight early and two late genes. The open reading frames (ORFs) of the virus genomes are designated E1 to E7 and L1 and L2, where "E" denotes early and "L" denotes late. L1 and L2 code for virus capsid proteins. The early (E) genes are associated with functions such as viral replication and cellular transformation.

The L1 protein is the major capsid protein and has a molecular weight of 55–60 kDa. L2 protein is a minor capsid protein which has a predicted molecular weight of 55–60 kDa and an apparent molecular weight of 75–100 kDa as determined by polyacrylamide gel electrophoresis. Immunologic data suggest that most of the L2 protein is internal to the L1 protein. The L2 proteins are highly conserved among different papillomaviruses, especially the 10 basic amino acids at the C-terminus. The L1 ORF is highly conserved among different papillomaviruses.

Recombinant L1 protein has been made in a variety of hosts, and under proper conditions self-assembles into virus-like particles (VLPs), either alone or in combination with L2. VLPs are candidates for a commercial vaccine. However, in order to be useful in a human vaccine, the VLPs must be highly purified and free from host cell contaminants. In the past, cross-flow ultrafiltration in a diafiltration mode has been used to remove contaminating biomolecules. However, this method resulted in the proteolytic degradation of the HPV L1. It would be desirable to have a L1 protein purification process which results in a highly pure, non-degraded product.

SUMMARY OF THE INVENTION

This invention relates to a method of purifying recombinant papilloma virus (HPV) virus-like particles (VLPs) comprising the steps of: contacting a partially purified VLP-containing cell lysate with a hydroxyapatite medium in a chromatography column, under conditions such that the VLPs bind to the hydroxyapatite medium; and eluting the bound VLPs with a solution comprising phosphate anions; and recovering the eluted VLPs.

The purification process can be used with VLPs which consist substantially of L1 protein, and it can also be used with VLPs which comprise L1 and L2 proteins. In addition it can be used with VLPs which are chimeric, i.e. contain L1 protein and a L2:fusion protein. In general, for vaccine use, VLPs which contain only L1 proteins are preferred.

The process is applicable to VLPs from virtually any strain of papillomavirus. It is preferred that a human papillomavirus (HPV) be used. Preferred strains of HPV are those which are known to cause the most serious diseases and conditions, including: HPV type 6a, HPV type 6b, HPV type 11, HPV type 16, HPV type 18, HPV type 31, HPV type 33, and HPV type 45.

In general, a host cell is transformed with a vector which encodes L1 or L1 and L2 proteins, or L1 and L2:fusion protein.

As used throughout the specification and claims, the term "L2: fusion protein" means that the DNA encoding the L2 protein has been operatively linked to another DNA encoding a desired protein, and preferably, another protein from HPV such as E1, E2, E3, E4, E5, E6 or E7. The L2 portion of the fusion protein may be full length, or it may have deletions and/or truncations. Examples may be found in co-pending U.S. Provisional Patent Application S. No. 60/096,638, (Attorney Docket Number 20276PV, which is hereby incorporated by reference) filed herewith.

The host cell may be any host cell which is easily cultured, as is known in the art, including yeast (*Saccharomyces cerevisiae*), insect cells, bacterial or mammalian cells. Yeast cells are particularly preferred.

The vector may also contain other elements as is known in the art, such as transcription and translation controlling elements and/or marker genes. The expressed L1, L1 and L2, or L1 and L2:fusion proteins will spontaneously assemble into VLPs. Host cells are typically lysed, and the cell lysate is then partially purified.

The partial purification step may include commonly used purification steps, and is not seen as a critical step in this invention. For example, the cell lysate may be subjected to a microfiltration process, and to at least one chromatography step, such as a cation-exchange chromatography.

It has been found, in accordance with this invention that a chromatography step, using hydroxyapatite as the column medium, followed by elution with a buffer solution containing phosphate anion, removes a large amount of contaminants from a partially purified cellular lysate. Specifically, it has been found that most contaminating biomolecules, including DNA, lipids and proteins are removed from the lysate.

In accordance with this invention, the final purified VLP preparation is generally at least 75% pure, preferably at least 80% pure, and more preferably at least 90% pure, as measured using the SDS/PAGE assay.

Virtually any commercially available hydroxyapatite column material may be used in this invention. It is preferable to use a ceramic hydroxyapatite which a particle size of approximately 20–50 μm and approximately an 800 Å pore size. One such commercially available hydroxyapatite is sold by BioRad as "Ceramic hydroxyapatite, Type II". However, others are effective as well.

In preparing the chromatography step of the purification process, it is recommended that the column feed be in a buffer with a pH of 6–8, and preferably approximately 7. A preferred buffer is 50 mM MOPS [3-(N-morpholino) propanesulfonic acid] at a pH of 7.0 and also containing 1.25 M NaCl.

Other buffer systems which may also be used are apparent to one of ordinary skill in the art and include: MES [2-(N-morpholino)ethanesulfonic acid]; BIS-TRIS [bis-(2-hydroxyethyl)-amino]tris-(hydroxymethyl)methane]; ADA [N-2-acetamidoiminodiacetic acid, monosodium salt]; ACES [N-2-acetamido-2-aminoethanesulfonic acid]; PIPES [piperazine-N,N'-bis(2-ethane-sulfonic acid)]; MOPSO [(3-N-morpholino)-2-hydroxypropane-sulfonic acid]; BIS-TRIS PROPANE [1,3-bis [tris(hydroxymethyl)methyl-amino]propane]; BES [N,N-bis-(2-hydroxyethyl)-2-amino-ethanesulfonic acid]; TES [N-tris(hydroxymethyl)methyl-2-aminoethane-sulfonic acid and 2-2([2-hydroxy-1,1-bis (hydroxymethyl)ethyl)amino]ethane sulfonic acid]; HEPES [N-2-hydroxyethylpiperazine-N'-2-ethane-sulfonic acid]; DIPSO [3-(N,N-bis(2-hydroxyethyl)amino)-2-hydroxy-propanesulfonic acid]; TAPSO [3-N-tris(Hydroxymethyl) methylamino]-2-hydroxy-propanesulfonic acid]; TRIS [tris-(hydroxymethyl)-aminomethane]; HEPPSO [N-(2-hydroxyethyl)-piperazine-N'-[2-hydroxy-propanesulfonic acid)]; POPSO [(piperazine-N,N'-bis[2-hydroxypropanesulfonic acid)]; EPPS [N-[2-Hydroxyethyl]-piperazine-N'-[3-propanesulfonic acid and HEPPS]; TEA [triethanolamine]; TRICINE [N[tris-(hydroxymethyl)methyl]glycine]; BICINE [N,N-bis-(2-hydroxyethyl]-glycine]; TAPS [3-{[tris-(hydroxymethyl) methyl]amino}-propane sulfonic acid]; imidazole; HEPPS [N-2-hydroxyethylpiperazine-N'-3-propane-sulfonic acid]; glycine amide, hydrochloride; glycylglycine; citrate; acetate; and succinate buffers.

The partially purified VLPs in the buffered solution is allowed to come into contact with the hydroxyapatite medium under conditions which allow the VLPs to bind to the hydroxyapatite. These conditions include a broad temperature range; room temperature is preferred. Flow rate may also vary greatly, and a preferred range is approximately 90 cm/hour.

After the VLPs are bound to the hydroxyapatite, the next step is recovery of the purified VLPs from the hydroxyapatite with an elution buffer. A preferred elution buffer solution contains a phosphate anion, such as a sodium or potassium phosphate solution. Preferred molar ranges are from about 0.05 M to about 1 M, with approximately. 0.2 M being preferred. The pH of the elution buffer should range from about pH 6–8, with a pH of about 7 being preferred.

Other advantages of the method of this invention include:
(a) no requirement for special chromatography equipment and techniques; (b) the method is rapid, requiring no buffer changes; and (c) the method provides an excellent yield of HPV L1.

The following non-limiting Examples are presented to better illustrate the invention.

EXAMPLES

Example 1

Preperation of Partially Purified Lysate

Yeast cells transformed to express VLPs were harvested and frozen for storage at −70° C. Frozen yeast cell suspension was removed from storage and thawed for approximately 3 hours at room temperature followed by approximately 18 hours at 4° C. BENZONASE® (Nycomed Pharma A/S, Copenhagen, Denmark) ($2.8 \times 10^5$ Units/mL and 0.21 mg protein/mL) was added to the cell suspension to a final concentration of 750 Units per gram of wet cell weight, and in one experiment was reduced to 335 Units per gram wet cell weight. Cells were stirred for 15 minutes, then disrupted by two passes through a sanitized APV Gaulin 30CD homogenizer at chamber pressures of 14,500 to 16,000 psi, resulting in 95% cell disruption. The remaining lysate was gently stirred for 18 hours at 4° C.

Clarification by microfiltration. Cell lysate was clarified by cross-flow microfiltration in a diafiltration mode as follows. Lysate was transferred to a sterile process tank with a 1-inch diameter inlet and outlet ports. The microfilter was a 0.65 micron pore size hollow-fiber filter cartridge of 5 square feet surface area (A/G Technologies #CFP-6-D-8A, Needham, Mass.) housed in an A/G Technologies Flex-Stand® Benchtop Pilot Hollow Fiber system. The retentate was diafiltered with 3 volumes of Diafiltration Buffer (below) to produce the clarified lysate. Diafiltration Buffer was 0.2 M ($Na^+$) MOPS, pH 7.0+0.4 M NaCl.

Chromatography of clarified lysate. The clarified lysate was fractionated by column chromatography using POROS® 50HS strong cation-exchange chromatography resin (PerSeptive Biosystems, Framingham, Mass.) packed in a chromatography column. The column was sanitized with 0.5 N NaOH prior to use. The column was equilibrated with HPV Diafiltration Buffer [0.2 M ($Na^+$)MOPS, pH 7.0+0.4 M NaCl] at room temperature. The cold (4° C.) clarified lysate was pumped onto the column at 125 mL/minute and the column was washed with 8 column volumes of room temperature HPV Column Buffer A [0.05 M ($Na^+$)MOPS, pH 7.0+0.5 M NaCl)] at 125 mL/minute with a linear gradient of 100% HPV Column Buffer A to 100% HPV Column Buffer B [0.05 M ($Na^+$)MOPS, pH 7.0+1.5 M NaCl]. Total linear gradient was 10 column volumes and was collected in 10 equal-volume fractions. Following the gradient, the column was washed with two column volumes of room temperature HPV Column Buffer B at 125 mL/minute which were collected in two additional fractions. Fractions were collected in sterile 2-liter plastic bottles and stored at 4° C. Fractions containing the last UV-absorbing peak (A280 nm and A230 nm) in the gradient were pooled, filtered using a MILLIPAK-200 disposable filter unit (Millipore, Bedford, Mass.) and stored at 4° C.

EXAMPLE 2

Hydroxyapatite Chromatography

All steps were carried out at room temperature. A chromatography column (13 mm ID×36 mm) packed with Ceramic Hydroxyapatite, Type II (BioRad Cat.#7320081, Hercules, Calif.), was pre-equilibrated in 50 mM MOPS, pH 7.0+1.25 M NaCl. The partially purified HPV solution from Example 1 was applied to the column at a linear flow rate of 90 cm/hour. After sample application was complete, the column was washed with eight column volumes of pre-equilibration buffer until the optical density of the column effluent was nearly zero. The HPV vaccine product was eluted with a 0% to 100% linear gradient of elution buffer (0.2 M sodium phosphate, pH 7.0+1.25 M NaCl), also at a linear flow rate of 90 cm/hour. The total volume of the gradient was four column volumes. Fractions containing the vaccine product were identified by RIA and Bradford protein assay. The protein concentration of the product was 100 µg/mL.

Assays: Bradford protein assays were performed using Coomassie Plus Assay Reagent (Pierce, Rockford, Ill.) using bovine serum albumin (BSA) as a standard. Lowry protein assays were performed according to the procedure of Lowry et al 1951 *J. Biol. Chem.* 193:265–270 using BSA as a calibration standard. Antigen was assayed by a multilayered ELISA using a monoclonal antibody that recognized a conformational epitope of the VLP. Microtiter plates-were coated with polyclonal goat anti-HPV VLP antibodies. Standard and test samples were diluted with PBS containing 1% w/v BSA, 0.1% TWEEN-20, and 0.1% sodium azide and were added to the wells where antigen was captured by the plate-bound antibodies. Monoclonal anti-HPV L1 VLP antibody (Chemicon, Temecula, Cailf.) was added to the wells to bind the antigen captured by the plate-bound antibodies. The monoclonal anti-HPV VLP antibodies were detected by horseradish peroxidase-conjugated anti-mouse IgG antibodies. A chromogenic substrate for horseradish peroxidase, 3,3', 5,5'-tetramethylbenzidine (Pierce) was added and absorbance at 450 nm was proportional to the concentration of L1 VLP in the sample.

The dynamic capacity of the column for the vaccine product was 2.9 mg-per mL of resin by Bradford, and 4.6 mg per mL of resin by RIA. Recovery through this step was 90% by Bradford protein assay or 82% by RIA when the column was loaded at 100% capacity. The recovery dropped to 63% by Bradford and 50% by RIA when the column was loaded at 8% capacity.

EXAMPLE 3

Removal of Other Biomolecules

A HPV 11 L1 sample prepared essentially as described in Examples 1 and 2 was assayed for the presence of DNA using a PCR-based assay. Results, which are presented in the table below, indicate that this chromatography method is highly effective in removing contaminating DNA from the final product.

| SAMPLE | protein (μg/mL) | DNA (pg/mL) | Ratio of pg DNA/ μg protein |
| --- | --- | --- | --- |
| Column Charge | 107 | 3270 | 30.6 |
| Flowthrough (fraction #6) | <10 | 196 | >19.6 |
| Eluate (fraction #20) | 230 | <2.6 | <0.011 |

EXAMPLE 4

Purification of a Chimeric VLP Purification of HPV Type 16 L1/L2$_{mini}$/E2 Chimeric VLPs Construction of the Modified L2 Gene YP3 Vector (Minimal L2)

This vector retains the coding sequences for the amino-terminal 69 amino acids and the carboxy-terminal 84 amino acids (aa) of HPV16 L2 which are fused in frame by a synthetic polylinker that introduces unique NotI, SacI, and XhoI restriction enzyme sites and results in the insertion of one glutamic acid residue and the mutation of a serine residue to glutamic acid.

PCR primers (Midland Certified Reagents) were designed to amplify L2 sequences from the native L2 gene contained within the vector, pGal110 HPV16 L1+L2.

Primers I (5'-CTT CCC CCC GGG CAC AAA ACA AAA TGC-3'; SEQ.ID.NO. 1) and C (5'-CTC GAG CTC GCG GCC GCC TGT ACC CGA CCC-3'; SEQ.ID. NO. 2) amplified a 265 bp sequence encoding the amino-terminal 69 aa and 23 bp of upstream untranslated sequence including a SmaI restriction enzyme site. Primer C modified and extended the L2 amino terminal-encoding region and appended NotI, SacI and XhoI restriction enzyme sites downstream of the L2 encoding sequences.

Primers A (5'-GCG GCC GCG AGC TCG AGG GTT ATA TTC CTG CAA ATA CAA-3'; SEQ.ID.NO. 3), C and D (5'-CCC TCC AGA TCT CTA GGC AGC CAA AGA GAC ATC TG-3'; SEQ.ID.NO. 4) amplified a 285 bp sequence encoding the carboxy-terminal 84 aa of L2 plus 6 bp which added a BglII restriction enzyme site. Primer A also appended a 17 bp sequence containing NotI, SacI, and XhoI sites upstream of the L2-encoding sequence.

The minimal L2 expression construct was assembled through the complementary sequences added by primers A and C. The isolated DNA products of the I/C and A/D amplification reactions above were both used in a PCR reaction which included I and D oligos as the amplifying primers. To facilitate the joining of the fragments through their 17 bp complementary sequence, three PCR cycles were performed with the annealing temperature at 37° C., followed by 15 cycles at 57° C. The resulting amplification product was blunt-end ligated into pcrScript (Stratagene, LaJolla) and transformed into XL-1 Blue MRF' cells (Stratagene, La Jolla). Positive clones were identified by PCR using primers I and D, and confirmed by restriction digest analysis. The construction was then verified by automated sequence analysis (Perkin Elmer, Inc., Foster City, Calif.).

Plasmid DNA from an appropriate isolate was then digested with SmaI and BglII; a fragment of approximately 0.5 kilobase pairs (kb) was gel purified and ligated with the 14 kb SmaI and BglII pGAL110 HPV16 L1 vector fragment. Competent DH5 *E. coli* cells (Gibco BRL, Rockville, Md.) were transformed with the ligation mixture and transformants selected on LB ampicillin plates (Remel, Lenexa, Kans.). Clones were initially screened by PCR in which primers D and I were used to amplify portions of L2; appropriate clones were then confirmed by restriction digestion analysis. Candidate clone YP3#1 was verified by sequence analysis as above.

YP3#1 was then employed as the backbone construct into which genes encoding HPV16 E1, E2 or E7 open reading frames were inserted.

Insertion of HPV E Protein-encoding Genes

The gene encoding HPV16 E2 was obtained by PCR amplification of a HPV16 positive clinical sample which was then inserted directly into the subdloning vector pCRII (Stratagene, La Jolla, Calif.) and sequence verified as above. The E2 gene sequence was then modified in the following manner:

1) In-frame XhoI, NaeI, NotI-containing DNA sequences were added to the amino terminal portion of E2. Additionally, NotI, NaeI, and XhoI-containing sequences were added to the carboxyl-terminal portion of E2 to facilitate insertion within E2 at the NotI, XhoI sites.

2) The DNA sequences were altered by PCR mutagenesis to encode alanine residues encode at residues glutamic acid 39 and isoleucine 73. This was designed to inactivate E2 protein function.

The modified HPV16 E2 gene described above was digested with NotI, XhoI and ligated with similarly digested YP3#1 vector. Transformants containing the properly-inserted E2 sequences were selected by PCR and sequence verified.

The same strategy was employed for the genes encoding HPV16 E1 and HPV16 E7. For E1, glycine 482 was altered to aspartic acid; for E7, cysteine 24 and glutamic acid 26 were both changed to glycine to inactivate protein function. The resultant constructs were then employed to transform yeast for expression analysis.

EXAMPLE 5

Identification and Growth of Yeast Expressing Chimeric VLPs

Plasmid DNA of YP3#1 and derivatives described above were used to transform *Saccharomyces cerevisiae* (MATa, leu2-04, prb1::HIS3, mnn9:URA3, cir°) by the spheroplast method (Hinnen et al., 1978, *Proc. Natl. Acad. Sci. USA* 75:1929–1933). Transformed spheroplasts were plated onto selective (leucine minus) medium (Remel, Lenexa, Kans.). Clones were isolated through two rounds of single colony selection. Small liquid cultures of candidate clones were grown to high cell density in medium containing galactose. Crude extracts were prepared by vigorous agitation with glass beads followed by centrifugation. The clarified extracts were analyzed for expression of L1, the L2 component, and VLPs by various methods including SDS PAGE, ELISA, immunoblotting, and ELA, using monoclonal antibodies or monospecific polyclonal antisera that recognize L1, or L2, or the amino or carboxy termini of L2, or L1 VLPs, or E1, or E2, or E7, or any other protein or peptide fused to the modified L2. Clones which expressed the L2 component and formed VLPs were selected for further characterization. One-liter or 16-liter cultures of selected clones were grown in galactose containing medium for large-scale preparation of chimerin VLPs.

Cell pellets were stored frozen at −70° C. Frozen cells (wet weight=148 g) were thawed and resuspended in 740 mL "Breaking Buffer" (200 mM MOPS, pH 7, 1 mM $CaCl_2$) to give approximately 20% (w/v) slurry. The nuclease BENZONASE® (Nycomed Pharma) was added to 750 units/g wet cell weight. The cell slurry was broken at a pressure of approximately 19,000 psi by 5 passes in a M110-Y Microfluidizer (Microflurdics Corp., Newton, Mass.). Cell slurry was collected and held on ice during breakage. Hematocrit assay indicated>80% breakage.

The aged cell lysate was clarified by microfiltration through a 0.65 micron pore size hollow-fiber cartridge (AIG Technologies) using a tangential-flow microfiltration apparatus run in a diafiltration mode. The lysate was diafiltered with three volumes of 0.25 M sodium citrate, 0.2 M MOPS, pH 7.0. Antigen passed through the membrane and was collected in the Permeate.

The diafiltered 0.65 mm permeate fraction (3.9 L) was loaded onto a 325 mL column (11.2 cm ID×3.3 cm) of POROS® 50HS resin (Perseptive Biosystems, Cambridge, Mass.) equilibrated in 200 mM MOPS, pH 7, 250 mM sodium citrate. The column was washed with 8 volumes of 50 mM MOPS, 0.5 M NaCl, 5 mM sodium phosphate, pH 7 and eluted with a 10 volume linear gradient from 0.5 to 1.5 M NaCl in the same buffer. Flow-thru and wash fractions were collected in bulk while 1 volume fractions were collected during elution. Column fractions were analyzed by western blotting and SDS-PAGE with colloidal Coomassie detection. Fractions containing predominantly p55 protein were pooled.

The 50HS pool was analyzed for total protein by BCA assay (Pierce). Based on the total protein (168 mg), a column of ceramic hydroxyapatite (HA) Type II (Bio-Rad) was poured to give 1 mL resin/2 mg protein. This column was 2.6 cm ID×15.7 cm. The column was equilibrated in 50 mM MOPS, pH 7, 1.25 M NaCl, 5 mM sodium phosphate. The 50HS pool (770 mL) was 0.22 mm filtered and applied to the HA column at a flow velocity of 113 cm/hr. Flow-thru was collected in bulk. The HA column was washed with 5 volumes of equilibration buffer and eluted with an 8 volume linear gradient from 5 to 200 mM sodium phosphate, pH 7 in 1.25 M NaCl. Fractions collected during the elution were analyzed by Western blot and SDS-PAGE with colloidal Coomassie detection. Fractions showing comparable purity and enrichment of L1 protein were pooled. The pooled fractions were filtered aseptically through a 0.22 mm membrane and stored at 4° C.

Process retains and product were analyzed for HPV 16 L1 using a specific EIA and for protein by BCA assay. Final purified product yield was 27 mg protein with a specific activity of 1.00 mg L1/mg protein. Electron microscopy confirmed the presence of intact VLP particles with a mean diameter of 32 nm. For SDS-PAGE purity analysis, an aliquot of final product was concentrated by TCA precipitation and analyzed by western blotting and SDS-PAGE with colloidal Coomassie detection. Quantitation of L1 was made using a 2.5 mg load and yeast contaminants were quantitated at 20.0 mg loading. The L1 protein was shown by densitometry to be>94% homogeneous. Co-purification of L1 and L2mini/E2 was demonstrated by specific immunoblotting analysis of process fractions.

What is claimed is:

1. A process for purifying recombinant papillomavirus virus-like particles (VLPs) comprising:
   (a) contacting a partially purified VLP-containing cell lysate with a hydroxyapatite medium in a chromatography column, under conditions such that the VLPs bind to the hydroxyapatite medium;
   (b) eluting the bound VLPs with a solution comprising phosphate anions; and
   (c) recovering the eluted VLPs.

2. A process according to claim 1 wherein the VLPs consist essentially of L1 protein.

3. A process according to claim 1 wherein the VLPs are human papillomavirus (HPV) VLPs.

4. A process according to claim 3 wherein the VLPs are selected from the group consisting of: HPV type 6a, HPV type 6b, HPV type 11, HPV type 16, HPV type 18, HPV type 31, HPV type 33, and HPV type 45.

5. A process according to claim 4 wherein the eluted VLPs are at least 75% pure.

6. A process according to claim 4 wherein the eluted VLPs are at least 90% pure.

7. A process according to claim 1 wherein the VLPs comprise L1 protein and a L2:fusion protein.

8. A process according to claim 7 wherein the L2:fusion protein has a L2 portion which is less than full length.

9. A process of making a purified human papillomavirus VLP product, suitable for use in a human vaccine comprising:
   (a) partially purifying a cell lysate, wherein the cell lysate is from yeast cells which have been transformed to express HPV L1 VLPs;
   (b) contacting the partially purified VLP-containing cell lysate with a hydroxyapatite medium in a chromatography column, under conditions such that the VLPs bind to the hydroxyapatite medium;
   (c) eluting the bound VLPs with a solution comprising phosphate anions; and
   (d) recovering the eluted VLPs.

\* \* \* \* \*

SEQUENCE LISTING

<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: PCR primer

<400> SEQUENCE: 1 cttcccccg ggcacaaaac aaaatgc                27

<210> SEQ ID NO 2

-continued

```
<211> LENGTH: 30
<212> TYPE: DNA
<213> ORGANISM: Artificial Sequence
<220> FEATURE:
<223> OTHER INFORMATION: PCR primer

<400> SEQUENCE: 2
ctcgagctcg cggccgcctg tacccgaccc                              30

<210> SEQ ID NO 3
<211> LENGTH: 39
<212> TYPE: DNA
<213> ORGANISM: Artificial Sequence
<220> FEATURE:
<223> OTHER INFORMATION: PCR primer

<400> SEQUENCE: 3
gcggccgcga gctcgagggt tatattcctg caaatacaa                    39

<210> SEQ ID NO 4
<211> LENGTH: 35
<212> TYPE: DNA
<213> ORGANISM: Artificial Sequence
<220> FEATURE:
<223> OTHER INFORMATION: PCR primer

<400> SEQUENCE: 4
ccctccagat ctctaggcag ccaaagagac atctg                        35
```